United States Patent [19]

Kersten et al.

[11] Patent Number: 4,931,466
[45] Date of Patent: Jun. 5, 1990

[54] CRYSTALLINE FORM AND ITS PREPARATION

[75] Inventors: Siegfried Kersten, Frankenthal; Karl-Friedrich Jaeger, Limburgerhof; Karl-Heinz Koenig, Frankenthal; Albrecht Muëller, Ludwigshafen; Josef B. Pawliczek, Speyer; Hans-Gert Recker, Ludwigshafen; Wolfgang Rohr, Wachenheim; August Wigger, Neuhofen, all of Fed. Rep. of Germany

[73] Assignee: BASF Aktiengesellschaft, Ludwigshafen, Fed. Rep. of Germany

[21] Appl. No.: 311,419

[22] Filed: Feb. 15, 1989

Related U.S. Application Data

[63] Continuation of Ser. No. 72,011, Jul. 10, 1987, abandoned.

[30] Foreign Application Priority Data

Jul. 19, 1986 [DE] Fed. Rep. of Germany ....... 3624437

[51] Int. Cl.$^5$ ...................... A01N 9/20; C07C 125/06
[52] U.S. Cl. ...................... 514/490; 560/132
[58] Field of Search ...................... 560/132; 514/490

[56] References Cited

U.S. PATENT DOCUMENTS 3,492,335 1/1970 Gubler ...................... 560/132

FOREIGN PATENT DOCUMENTS 2231249 1/1974 Fed. Rep. of Germany .
1426233 2/1976 United Kingdom .

OTHER PUBLICATIONS

Römpps Chemie-Lexikon, Neumüller, Frankh'sche Verlagshandlung Stuttgart.
Hackh's Chemical Dictionary, McGraw-Hill Book Company, Inc. Advanced Inorganic Chemistry, Interscience Publishers F. Albert Cotton et al.
X-ray Spectra of the Two Different Modification I and II of Cloethocarb.

*Primary Examiner*—Bruce D. Gray
*Attorney, Agent, or Firm*—Keil & Weinkauf

[57] ABSTRACT

A compound of the chemical formula (I)

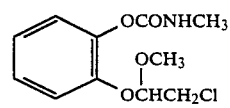

in a specific crystalline form, processes for its preparation, and its use for pest control.

8 Claims, No Drawings

CRYSTALLINE FORM AND ITS PREPARATION

This application is a continuation of application Ser. No. 072,011, filed on July 10, 1987 now abandoned.

The present invention relates to the crystalline form of 2-(2-chloro-1-methoxyethoxy)-phenyl methylcarbamate I which melts at 79° C., a process for its preparation and its use for controllintg pests.

Compound I is an insecticidal active ingredient known under the common name cloethocarb (DE-C-22 31 249); its formulations is solid form, for example granules having sand or corncob cores, and also suspension concentrates (SC) undergo changes which, particularly in the case of solids, and even in the raw material, manifest themselves as caking or agglomeration. However, the process is not due to, for example, hydroscopic behavior but has other causes. Cloethocarb can in fact occur as various crystalline forms, depending on the precipitation condition or the choice of solvent. DebyeScherrer photographs show that these forms differ only slightly. The crystals of the various forms all belong to the triclinic system.

We have found that a crystalline form of compound I which melts at 79° C. does not exhibit the property of agglomeration.

Differential thermal analysis (DTA) show differences of 1°-2° C. in the melting points of industrial products, and a higher-melting modification of cloethocarb (M I) having a melting point of 79° C. and a lower-melting form (M II) having a melting point of 77° C. can be detected (the designations M I and M II have been chosen freely).

Solid-state NMR spectra likewise show small differences in the position of some signals for the forms M I and M II. In the spectra of mixtures of the forms, these signals are no longer separated, and the ratio of the forms in the mixture cannot be determined.

The present invention has the following effect: a formulated product containing cloethocarb of form M II changes during storage, particularly at elevated temperatures (40°-60° C.): the formulated product exhibits effluorescence, and the effluorescent crystals become entangled with one another and thus cause agglomeration of the material, so that uniform discharge of the product is no longer ensured. During this process, cloethocarb undergoes a transformation from form M II to form M I.

In the SC formulation too, recrystallization in the aqueous suspension is observed when form II is present, so that the formulation is destroyed.

Cloethocarb of form M I does not exhibit this effluorescence, and both solid formulations, e.g. granules having a core (with sand or corncobs as a carrier), and the SC formulation remain unchanged during storage and can subsequently be applied satisfactorily.

It is an object of the present invention to prepare cloethocarb in the correct form M I, for the formulation. It is very important to obtain cloethocarb in form M I without contamination with form M II, since even small amounts of the latter form lead to the effluorescence described.

We have found that this object is achieved, and that cloethocarb is obtained as form M I in the novel process, if the cloethocarb/methylene chloride solution present at room temperature is mixed with heptane at 65°-70° C. so that the mixture reaches 55°-60° C., and the subsequent crystallization is carried out by cooling from this temperature. Feeding with form M I is in general not necessary but may be advantageous in specific cases. Crystallization may also be achieved by heating cloethocarb in a solvent mixture consisting of methylene chloride and heptane in a volume ratio of from 1:5 to 1:30 and then allowing the mixture to cool slowly.

Instead of methylene chloride, which is preferred, chlorohydrocarbons, such as chloroform, carbon tetrachloride, 1,1-dichloroethane, 1,2-dichloroethane, 1,1,1-trichloroethane, 1,1,2-trichloroethane, 1,1,2,2-tetrachloroethane and ethylene chloride, aromatic hydrocarbons, such as benzene, toluene and the xylenes, aromatic chlorohydrocarbons, such as chlorobenzene and the dichlorobenzenes, and ethers, such as dimethyl ether, diethyl ether, diisopropyl ether, methyl tert-butyl ether, furan, tetrahydrofuran and dioxane, can also be used. From 15 to 60 kg of cloethocarb can be dissolved in 100 liters of one of these solvents.

Instead of heptane, which is preferred, other acyclic and cyclic hydrocarbons, such as n-pentane, n-hexane, n-heptane, n-octane and the pentane, hexane, heptane and octane isomers and their isomer mixtures, petroleum ether, cyclopentane, cyclohexane, cycloheptane and cyclooctane, can also be used.

In another novel process which likewise gives form M I of the structure according to the invention, aqueous acetone solutions of cloethocarb are precipitated with water. In practice, for example, cloethocarb is dissolved in acetone and precipitated with water at below room temperature (e.g. from 5° to 10° C.).

Finally, the transformation of M II or mixtures of M I and M II can also be forced, according to the invention, by the intensive action of mechanical means, for example rubbing or stirring.

The examples which follow illustrate the process according to the invention.

1. Precipitation of a solution of cloethocarb in methylene chloride with heptane at 65°-70° C. in a mixing zone.

In the course of one hour, 1,000 l of heptane are heated to 65°-70° C. and mixed with 110 l of a solution of about 38-40 kg of cloethocarb in methylene chloride at 20° C., the said mixing procedure being carried out in a mixing zone filled with Raschig rings. The temperature at the outlet of the mixing zone reaches 55°-60° C. The crystallization kettle is heated beforehand to 55°-60° C. so that the crystallization can begin at 55° C.

Further cooling can be effected by reducing the pressure, i.e. evaporative cooling, or by cooling via the kettle shell.

After filtration or centrifuging and drying, a product which is shown by differential thermal analysis to be pure cloethocarb of form M I is obtained.

2. Precipitation of a solution of cloethocarb in methylene chloride with n-heptane at 65°-70° C. (heptane initially taken)

If n-heptane is initially taken and heated to 65°-70° C. and the solution of cloethocarb in methylene chloride (20° C.) is added, a mixing temperature of 55° C. is reached. The cloethocarb which crystallizes out is in the form of the pure form M I (DTA).

Comparison

Precipitation of a solution with cold heptane (modification M II)

(a) Precipitation of a solution of cloethocarb in methylene chloride with n-heptane at 15°-30° C. gives cloethocarb of form M II (DTA measurements).

(b) If the solution is seeded with crystals of form I, cloethocarb is obtained as a mixture of forms M I and M II (DTA measurements) in the precipitation with cold heptane.

3. Precipitation of a solution of cloethocarb in acetone with water

If a solution of cloethocarb and acetone at 5°-10° C. is introduced into water, cloethocarb crystallizes out as form M I (DTA measurements).

4. Transformation of cloethocarb of form M II into form M I in the crystalline state (a) By thorough mixing in a stirred suction filter at from 55° to 60° C. over a period of 16 hours, it is possible to transform cloethocarb from form M II into form M I (DTA measurements).

(b) If the same experiment is carried out without stirring, i.e. the material is only heated at 55°-60° c., no transformation of form M II into form M I takes place (DTA measurements).

We claim:

1. A compound of the chemical formula I

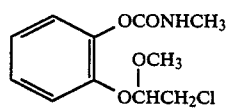

which consists essentially of the compound in its crystalline form which melts at 79° C.

2. A process for the preparation of a crystalline material consisting of compound I as defined in claim 1, wherein compound I is dissolved in methylene chloride, the solution is brought to below 40° C. and mixed with excess n-heptane at about 65°-70° C. so that a mixing temperature of about 55°-60° C. results, and, after cooling, compound I having the form which melts at 79° C. is isolated.

3. A process for the preparation of a crystalline material consisting of compound I as defined in claim 1, and having the crystalline form which melts at 79° C. which comprises: dissolving compound I in acetone at 5°-10° C. and introducing the solution into water, whereby the component I is converted to the form which melts at 79° C.

4. A process for the preparation of a crystalline material consisting of compound I as defined in claim 1, wherein the crystalline form of I which melts at 77° C. is heated at 55°-60° C. to form the form which melts at 79° C.

5. A pesticidal composition consisting essentially of a conventional carrier and the crystalline form of I which melts at 79° C. as defined in claim 1.

6. The pesticidal composition of claim 5, which contains from 0.1 to 95% by weight of the crystalline form of I which melts at 79° C.

7. A method of controlling pests, wherein the pests and/or the areas and/or rooms to be kept free of pests are treated with the crystalline form of I which melts at 79° C. as defined in claim 1, in an amount which is effective against pests.

8. The compound of the formula I

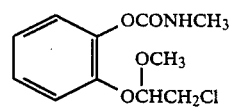

which consists essentially of the compound in its crystalline form which melts at 79° C. produced (a) by a process in which compound I is dissolved in methylene chloride, the solution is brought to below 40° C. and mixed with excess n-heptane at about 65°-70° C. so that a mixing temperature of about 55°-60° C. results, and, after cooling, isolating said compound I having the crystalline form which melts at 79° C., or (b) by a process in which compound I is dissolved in acetone and the solution is introduced into water at 5°-10° C., or (c) the crystalline form of the compound I which melts at 77° C. is heated at 55°-60° C. to form the crystalline form of compound I which melts at 79° C.

* * * * *